(12) United States Patent
Zimmer et al.

(10) Patent No.: US 11,863,941 B2
(45) Date of Patent: Jan. 2, 2024

(54) AUDITORY FILTER FITTING FOR HEARING DEVICES

(71) Applicants: Anhui Huami Health Technology Co., Ltd., Hefei (CN); Zepp, Inc., Cupertino, CA (US)

(72) Inventors: Aaron Zimmer, Vancouver (CA); Aiden Arnold, Comox (CA); Artem Galeev, Vancouver (CA); Yan Vule, Port Moody (CA); Kongqiao Wang, Hefei (CN)

(73) Assignees: Anhui Huami Health Technology Co., Ltd., Anhui FTZ (CN); Zepp, Inc., Cupertino, CA (US)

( * ) Notice: Subject to any disclaimer, the term of this patent is extended or adjusted under 35 U.S.C. 154(b) by 0 days.

(21) Appl. No.: 17/715,606

(22) Filed: Apr. 7, 2022

(65) Prior Publication Data

US 2023/0328467 A1  Oct. 12, 2023

(51) Int. Cl.
*H04R 25/00* (2006.01)

(52) U.S. Cl.
CPC ............ *H04R 25/70* (2013.01); *H04R 25/50* (2013.01)

(58) Field of Classification Search
CPC ......... H04R 25/00; H04R 25/50; H04R 25/70
See application file for complete search history.

(56) References Cited

U.S. PATENT DOCUMENTS

| 10,398,360 | B1* | 9/2019 | Clark ................. H03G 9/025 |
| 2007/0156063 | A1* | 7/2007 | Zoth ................. A61B 5/126 |
| | | | 600/559 |
| 2021/0105565 | A1 | 4/2021 | Pedersen et al. |
| 2021/0185465 | A1 | 6/2021 | Bramslow |

OTHER PUBLICATIONS

Yoshua Bengio et al.; GFlowNet Foundations; arXiv:2111.09266v1 [cs.LG]; Nov. 17, 2021; pp. 1-70.
Josef Schlittenlacher et al.; Application of Bayesian Active Learning to the Estimation of Auditory Filter Shapes Using the Notched-Noise Method; 2019 ISAAE special collection: Original Article; Trends in Hearing vol. 24: 1-13; pp. 1-13.

* cited by examiner

*Primary Examiner* — Suhan Ni
(74) *Attorney, Agent, or Firm* — Young Basile Hanlon & MacFarlane, P.C.

(57) ABSTRACT

A system and methods are used to enable hearing device calibration using auditory filters. The system and methods are used to reduce processing time for estimating auditory filters for new hearing device users and can be performed by the user without the aid of an audiologist. The system and methods use a database of notched-noise test results of other users to create a prior distribution of possible auditory filter parameters. The prior distribution is used to minimize the number of notched-noise test performed, thereby reducing the amount of calibration time.

17 Claims, 6 Drawing Sheets

AUDITORY FILTER FITTING FOR HEARING DEVICES

TECHNICAL FIELD

This disclosure relates to systems and methods for hearing devices.

BACKGROUND

Conventional hearing devices are programmed by an audiologist using real ear measurements to have frequency dependent gains that match the pure tone test results of the subject (i.e., user). Pure tone audiograms provide individualized thresholds of hearing for a small number of standardized frequencies (usually less than 10). Both the coarseness of the audiogram measurements and the lack of information about interference between different frequency bands limits the extent to which hearing devices can be personalized to a specific user. Methods and systems are needed to remove these limitations and make it possible to optimize the hearing device calibration beyond what is currently available.

SUMMARY

Disclosed herein are implementations of methods and systems for auditory filter fitting for hearing devices. In an aspect, a system may include a database, a computing device, and a hearing device. The database may be configured to store notched-noise test results of multiple users. The computing device may be configured to obtain the notched-noise test results of the multiple users. The computing device may be configured to generate a probabilistic model of auditory filters based on the notched-noise test results of the multiple users. The computing device may be configured to select a signal to test based on the probabilistic model of auditory filters. The computing device may be configured to transmit signal parameters based on the selected signal to test. The hearing device may be configured to receive the signal parameters. The hearing device may be configured to convert the signal parameters to an audio signal. The hearing device may be configured to transmit the audio signal.

In an aspect, a computing device may include a processor, an auditory filter processor, a signal selector, and a transmitter. The processor may be configured to obtain notched-noise test results of multiple users from a database. The auditory filter processor may be configured to generate a probabilistic model of auditory filters based on the notched-noise test results of the multiple users. The signal selector may be configured to select a test signal based on the probabilistic model of auditory filters. The transmitter may be configured to transmit signal parameters based on the selected test signal.

In an aspect, a method may include obtaining notched-noise test results of multiple uses from a database. The method may include generating a probabilistic model of auditory filters based on the notched-noise test results of the multiple users. The method may include selecting a test signal based on the probabilistic model of auditory filters. The method may include transmitting signal parameters based on the selected test signal.

In one or more aspects, the computing device may be configured to receive a user response in response to the audio signal. In one or more aspects, the computing device may be configured to update the probabilistic model of auditory filters based on the received user response. In one or more aspects, the computing device may be configured to update the probabilistic model of auditory filters based on notched-noise test results of a subset of the multiple users. In one or more aspects, the subset of the plurality of uses may be determined based on the received user response. In one or more aspects, the audio signal may be a notched-noise signal. In one or more aspects, the computing device may be configured to use a Bayesian optimal experimental design to select the signal to test. In one or more aspects, the computing device may include an interface configured to obtain the user response.

In one or more aspects, the method may include obtaining a user response. In one or more aspects, the method may include updating the probabilistic model of auditory filters based on the user response. In one or more aspects, the method may include updating the probabilistic model of auditory filters based on notched-noise test results of a subset of the multiple users. In one or more aspects, the method may include determining the subset of the multiple users based on the user response. In one or more aspects, the method may include selecting the test signal using a Bayesian optimal experimental design. In one or more aspects, the method includes transmitting the signal parameters to a hearing device for auditory filter fitting of the hearing device.

BRIEF DESCRIPTION OF THE DRAWINGS

The disclosure is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity.

DETAILED DESCRIPTION

Figure 1:
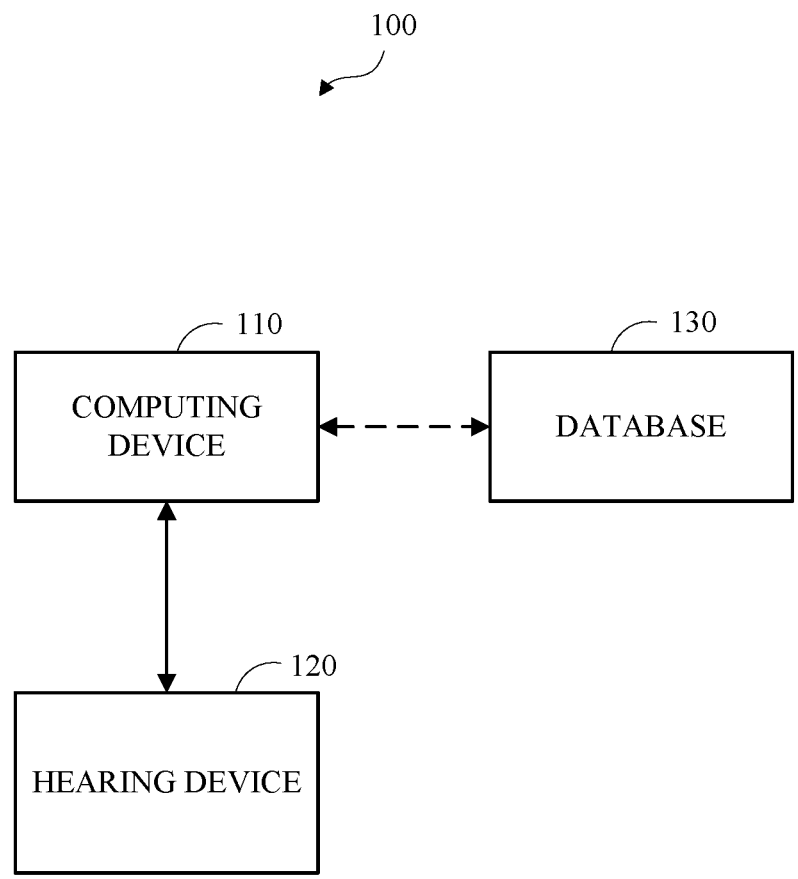
FIG. 1 is a block diagram of an example of an auditory filter fitting system.

Embodiments described herein may use auditory filters instead of audiograms to optimize hearing device calibration. The auditory filters may be asymmetrical such that the bandwidth is different on the side left of center and the side right of center. Accordingly, 3 parameters are required to describe each auditory filter instead of 2 parameters. The additional parameter substantially increases the duration of the hearing device fitting when compared to a pure tone audiometry where the number of parameters per frequency is 1. The search space becomes $N^3$ for auditory filters compared to N for pure tone audiometry, where N is the number of frequency bins. The embodiments described herein may be used to reduce processing time for estimating auditory filters for new hearing device users and can be performed by the user without the aid of an audiologist. Auditory filters may be used to model the way that sound is transmitted to the brain by the cochlea. Auditory filters can directly model the frequency response of the basilar membrane. Changes in the frequency response of the basilar membrane correspond to different types of sensorineural hearing impairment. As a result, the hearing impairment of an individual can be better characterized by auditory filters than by audiograms. Therefore, the auditory filter models generated by the embodiments described herein can be used to optimize the hearing device outputs for each individual user. For example, the sound emitted by the hearing device can be altered to automatically maximize the intelligibility of the sound based on the auditory filter for that specific user as well as an empirical model of intelligibility, without requiring feedback from the user.

The auditory filters provide much more information about the characteristics of a hearing device user's unique hearing loss compared to a standard audiogram. For example, auditory filters may characterize loss of resolution and sensitivity for detecting sounds of different frequencies. Auditory filters may be used to characterize loss in temporal resolution for sounds of a given frequency. Accordingly, auditory filters can be used to improve hearing device personalization. However, auditory filters are not currently used in the hearing device fitting process since it is much more time consuming when compared to traditional audiometric tests.

The embodiments described herein sufficiently reduce the fitting duration to make the auditory fitting procedure scalable by using a large database of notched-noise test results of other users to create a prior distribution of possible auditory filter parameters. This prior distribution combined with the notched-noise test results of the user may be used to minimize the number of notched-noise tests performed while maximizing the accuracy and precision of the auditory filter parameters for the current user.

The embodiments described herein may use a Bayesian optimal experimental design to minimize the number of notched-noise tests performed while maximizing the accuracy and precision of the auditory filter parameters for the current user. Bayesian optimal experimental design is a framework for minimizing the number of measurements that are required to estimate the parameters of a model. The goal of the Bayesian optimal experimental design is to increase the amount of useful information that each measurement provides while taking into account the information provided by all previous measurements. The embodiments described herein use this framework to sequentially select a notched-noise test stimulus to audibly present to the user of the hearing device in order to minimize the number of measurements required to parameterize their auditory filters while also considering all previous available data, including data from other users.

The data from other users can be used to constrain the model parameters since there may be similarities in the patterns of hearing loss for different groups of people. There are many possible ways to derive the prior distribution from the database of other users' data in order to employ Bayesian optimal experimental design for this problem. For instance, given a large enough database, a deep neural network can be used to encode the prior distribution by training to estimate the auditory filter parameters from the same notched-noise measurement data currently available in the fitting procedure (i.e. learning to estimate auditory filter parameters from limited data).

FIG. 1 is a block diagram of an example of an auditory filter fitting system 100. The auditory filter fitting system 100 includes a computing device 110, a hearing device 120, and a database 130.

The computing device 110 may a stationary device, such as a desktop computer, or a mobile device, such as a mobile phone, a smartphone, a tablet computing device, a laptop, or any other portable computing device. The computing device is configured to run an application. The application may be a software application that enables an accurate fitting procedure for the hearing device 120 that allows greater adaptability of the hearing device 120 to individual users by replacing audiograms as the measure of hearing loss with the more detailed auditory filters based measure of hearing loss. The application enables the computing device 110 to determine an auditory filter model based on user responses and estimate one or more auditory filters, which can be used to calibrate the hearing device 120.

The computing device 110 is configured to communicate with the database 130, for example, via a network such as the Internet. In some examples, the database 130 may be stored on a memory of the computing device 110. The database 130 is configured to store notched-noise test results of one or more users. For example, the database may include notched-noise test results of a large pool of users, for example, all users of the auditory filter fitting system 100. In some examples, the database may include notched-noise test results of users that are not associated with the auditory filter fitting system 100.

The computing device 110 is configured to obtain notched-noise test result data from the database 130. In some examples, the obtained notched-noise test result data may be data associated with users that have a similar hearing profile as the user of the hearing device 120. The computing device 110 is configured to determine and/or update a probabilistic model of the auditory filters of the user of the hearing device 120.

The computing device 110 is configured to communicate with the hearing device 120 through a wired or wireless connection, such as Bluetooth, wireless fidelity (WiFi), near-field communications (NFC), or any other suitable short range wireless communication protocols. The computing device 110 is configured to determine a test signal to reduce the uncertainty in an auditory filter. The computing device 110 may be configured to use a Bayesian optimal experimental design to determine the test signal. The computing device 110 may be configured to select an experiment to minimize the expected model uncertainty after the measurement is performed. The test signal may be based on the probabilistic model of the auditory filters of the user of the hearing device 120. For example, for each possible experiment, the computing device 110 may compute the probability of each outcome of that experiment in terms of its effect on the auditory filter model posterior distribution and select the experiment that on average reduces the model uncertainty the most. Alternatively, the test signal may be determined based on a decrease in entropy from the prior distribution (i.e., before the single notched-noise threshold measurement) to the posterior distribution (i.e., after the single notched-noise threshold measurement) or the expected informational gain. In this example, the computing device 110 may obtain the prior probability distribution of the outcomes of the experiment for every possible experiment. From these outcomes, the computing device 110 may compute the distribution of the posterior distribution of the model parameters for each possible experiment and select the experiment that produces the posterior distribution with the minimum uncertainty or entropy on average. These distributions may be learned using a neural network, such as a deep neural network, a convolutional neural network, a recurrent neural network, or other neural network. In an example, the neural network may be trained directly to select the optimal experiment to perform based on the current model distribution or a model may be trained to predict the effect of running a specific experiment on a specific model distribution and search for the optimal experiment based on the prediction outputs of the neural network. These prediction models may be trained by splitting the database into pairs of inputs and outputs where the inputs may be the prior model distributions before an experiment was run and the type of experiment and the outputs may be the prior model distributions after the experiment was run. The computing device 110 is configured to transmit signal parameters associated with the determined test signal to the hearing device 120.

The hearing device 120 is configured to receive the signal parameters from the computing device 110. The hearing device 120 is configured to convert the signal parameters to an audio signal. The audio signal may be a notched-noise signal. The hearing device 120 may be configured to apply calibration parameters of the hearing device 120 to the audio signal and transmit the audio signal via a speaker of the hearing device 120. The audio signal is transmitted to obtain a response from a user of the hearing device 120. The response may be obtained from the computing device 110, for example, via a user input. The user input may include a touch or gesture input on a display of the computing device 110 or a voice input from a microphone of the computing device 110. The computing device 110 may update the probabilistic model of the auditory filters based on the user input, determine a notched-noise test result based on the user input, store the notched-noise test result, or any combination thereof.

Figure 2:
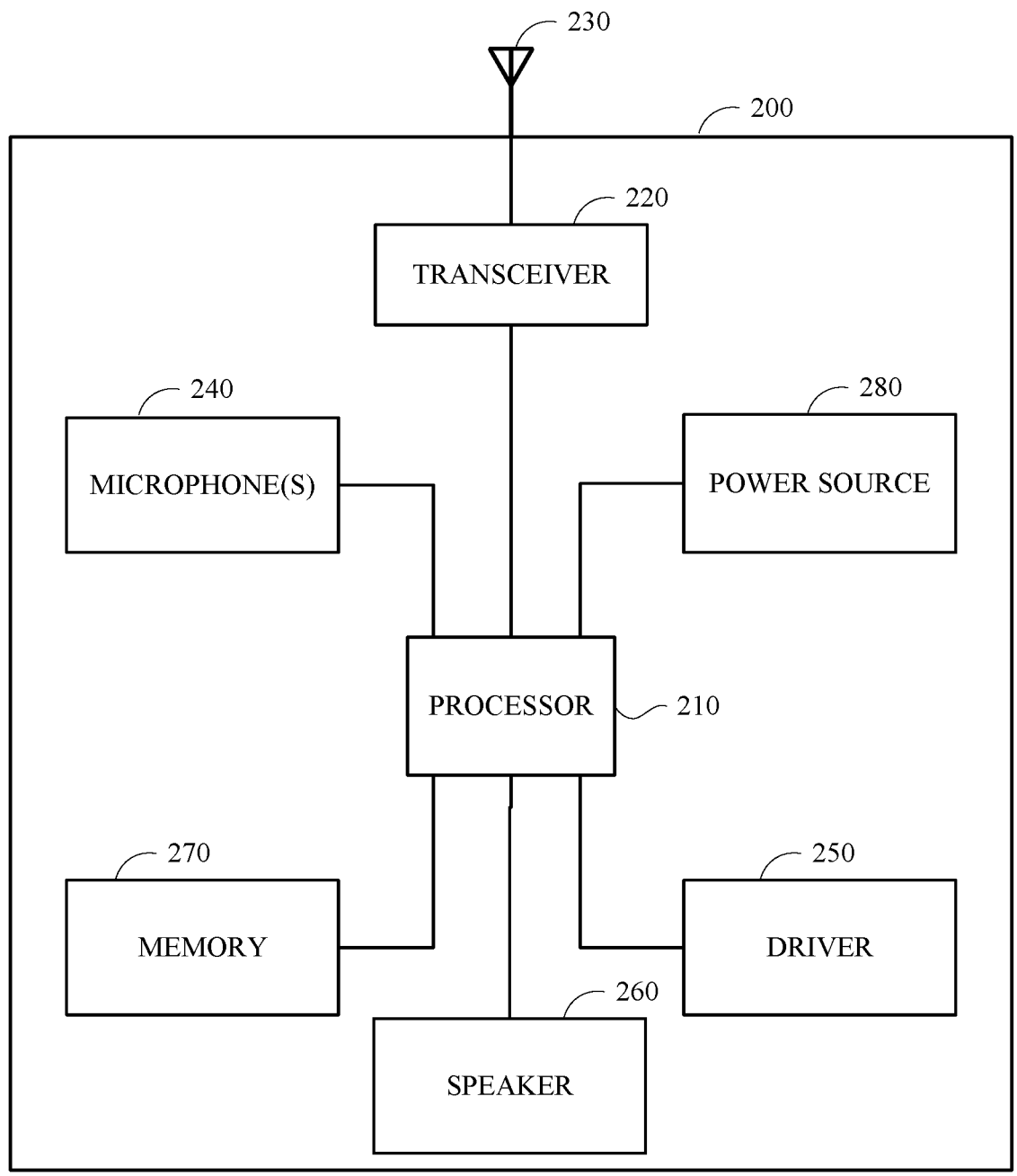
FIG. 2 is a block diagram of an example of a hearing device for use in the auditory filter fitting system shown in FIG. 1.

FIG. 2 is a block diagram of an example of a hearing device 200 for use in the auditory filter fitting system 100 shown in FIG. 1. The hearing device 200 may be a small device that fits in or on the ear of a user and configured to be worn by a partially deaf person to amplify sound. The hearing device 200 includes a processor 210, a transceiver 220, an antenna 230, one or more microphones 240, a driver 250, a speaker 260, a memory 270, and a power source 280.

The processor 210 may be a general purpose processor, a special purpose processor, a conventional processor, a digital signal processor (DSP), one or more microprocessors, one or more microprocessors in association with a DSP core, a controller, a microcontroller, one or more Application Specific Integrated Circuits (ASICs), one or more Field Programmable Gate Array (FPGAs) circuits, any other type of integrated circuit (IC), a state machine, or any other processing device. The processor 210 may perform signal coding, data processing, power control, input/output processing, and/or any other functionality that enables the hearing device 200 to produce notched-noise signals for auditory filter fitting. The processor 210 may be coupled to the transceiver 220, which may be coupled to the antenna 230. While FIG. 2 shows the processor 210 and the transceiver 220 as separate components, in some embodiments, the processor 210 and the transceiver 220 may be integrated together in an electronic package or chip. The processor 210 may be configured to execute instructions stored on a non-transitory computer readable medium, such as the memory 270.

The transceiver 220 may be configured to modulate the signals that are to be transmitted by the antenna 230 and to demodulate the signals that are received by the antenna 230.

The antenna 230 may be configured to transmit signals and receive signals over an air interface. For example, the antenna 230 may be configured to transmit and/or receive RF signals. In an embodiment, the antenna 230 may be configured to transmit and/or receive Bluetooth, WiFi, NFC, or any other suitable short range wireless signals, for example. It will be appreciated that the antenna 230 may be configured to transmit and/or receive any combination of wireless signals.

The processor 210 may be coupled to, and may receive electrical signals from the one or more microphones 240. The one or more microphones 240 are configured to detect sound, convert the detected sound to an electrical signal, and transmit the electrical signal to the processor 210. The one or more microphones 240 may include a directional microphone, an omnidirectional microphone, or both. Directional microphones are configured to detect sound from the front of the user which can be helpful to understand conversation in a noisy environment. Omnidirectional microphones are configured to detect sound from every direction and provide the user a real-time experience.

The processor 210 is configured to receive the electrical signal from the one or more microphones 240. The processor 210 is configured to receive the electrical signals from the one or more microphone 240 and convert the electrical signals to a digital signal. In some examples, the processor 210 is configured to transmit the digital signal to the driver 250.

The driver 250 is configured to adjust the digital signal according to the requirements of the user, for example based on one or more signal parameters received from a computing device, such as computing device 110 shown in FIG. 1. The driver 250 is configured to amplify the digital signal based on the hearing profile of the user. The driver 250 may be configured to apply calibration weights to the digital signal and convert the digital signal to an audio signal, for example, an analog audio signal. The driver 250 is configured to transmit the audio signal to the speaker 260. In some examples, the driver 250 may be combined with the processor 210. The speaker 260 is configured to receive the audio signal from the driver 250 and output a sound based on the audio signal.

The processor 210 may access information from, and store data in, any type of suitable memory, such as the memory 270. The memory 270 may include random-access memory (RAM), read-only memory (ROM), a hard disk, a subscriber identity module (SIM) card, a memory stick, a secure digital (SD) memory card, or any other type of memory storage device. In an embodiment, the processor 210 may access information from, and store data in, the memory 270 such as, for example, calibration weights, hearing profiles, firmware to operate the hearing device 200, or any combination thereof.

The processor 210 may receive power from the power source 280, and may be configured to distribute and/or control the power to the other components of the hearing device 200. The power source 280 may be any suitable device for powering the hearing device 200. For example, the power source 280 may include one or more dry cell batteries (e.g., nickel-cadmium (NiCd), nickel-zinc (NiZn), nickel metal hydride (NiMH), lithium-ion (Li-ion)), solar cells, fuel cells, and the like.

Figure 3:
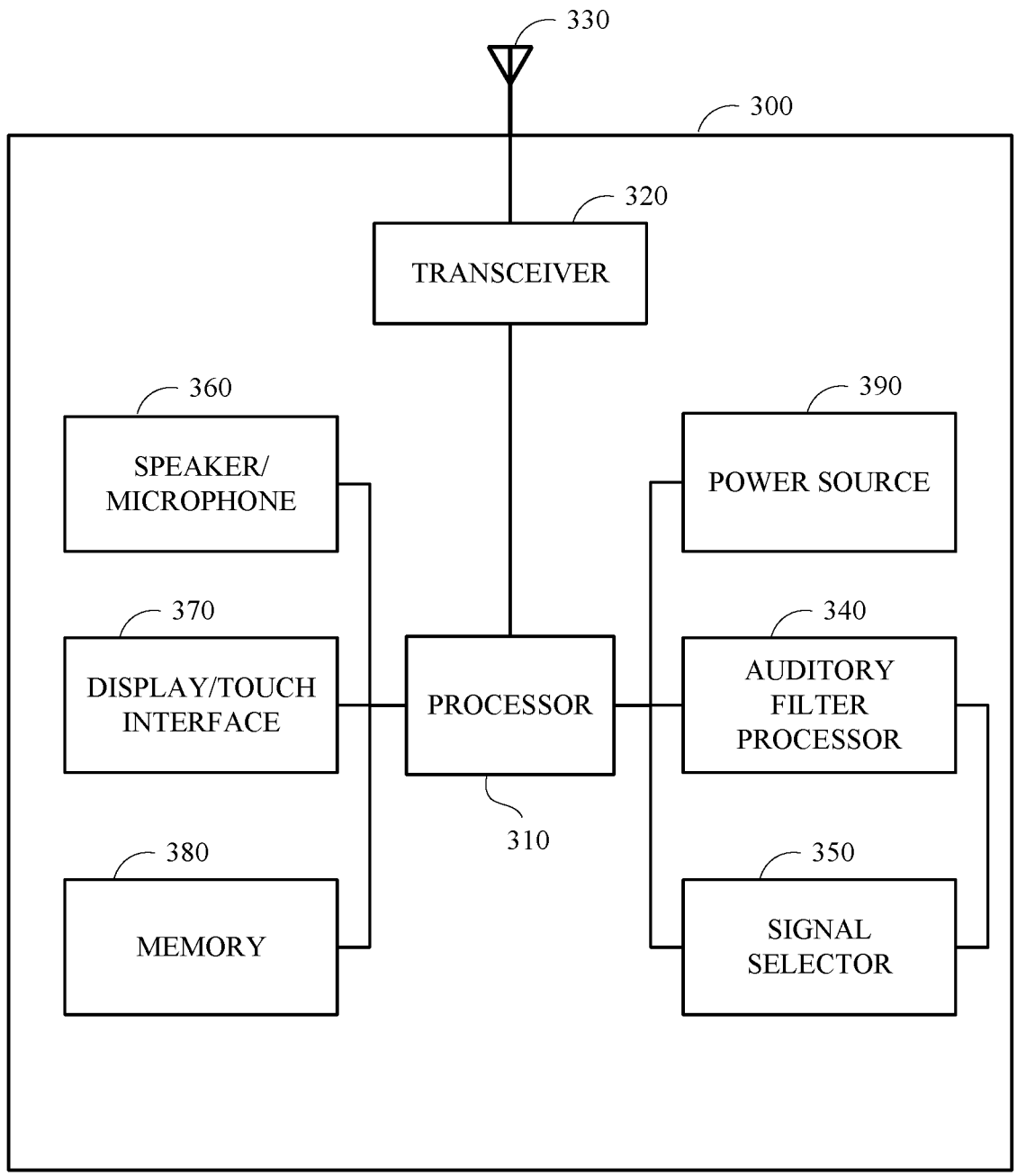
FIG. 3 is a block diagram of an example of a computing device for use in the auditory filter fitting system shown in FIG. 1.

FIG. 3 is a block diagram of an example of a computing device 300 for use in an auditory filter fitting system, such as the auditory filter fitting system 100 shown in FIG. 1. The computing device 300 may be a desktop computer or a mobile device, such as a mobile phone, a smartphone, a tablet computing device, a laptop, or any other portable computing device. As shown in FIG. 3, the computing device 300 includes a processor 310, a transceiver 320, an antenna 330, an auditory filter processor 340, and a signal selector 350, a display/touch interface 370, a speaker/microphone 360, memory 380, and a power source 390. In some examples, the transceiver may be implemented as individual components, such as a transmitter and a receiver.

The processor 310 may be a general purpose processor, a special purpose processor, a conventional processor, a DSP, one or more microprocessors, one or more microprocessors in association with a DSP core, a controller, a microcontroller, one or more ASICs, one or more FPGAs circuits, any other type of IC, a state machine, or any other processing device. The processor 310 may perform signal coding, data processing, power control, input/output processing, and/or any other functionality that enables the computing device 300 to model auditory filters for fitting a hearing device, such as hearing device 200 shown in FIG. 2. The processor 310 may be coupled to the transceiver 320, which may be coupled to the antenna 330. While FIG. 3 shows the processor 310 and the transceiver 320 as separate components, in some embodiments, the processor 310 and the transceiver 320 may be integrated together in an electronic package or chip. The processor 310 may be configured to execute instructions stored on a non-transitory computer readable medium, such as memory 380.

The transceiver 320 may be configured to modulate the signals that are to be transmitted by the antenna 330 and to demodulate the signals that are received by the antenna 330.

The antenna 330 may be configured to transmit signals and receive signals over an air interface. For example, the antenna 330 may be configured to transmit and/or receive RF signals. In an embodiment, the antenna 330 may be configured to transmit and/or receive Bluetooth, WiFi, NFC, or any other suitable short range wireless signals, for example. It will be appreciated that the antenna 330 may be configured to transmit and/or receive any combination of wireless signals.

The processor 310 may be coupled to the auditory filter processor 340. The auditory filter processor 340 is configured to obtain notched-noise test results for one or more users from a database (not shown). The database may be an external database that can be accessed via a wired or wireless connection, for example via the antenna 330. In some examples, the database may be stored on the memory 380. The database may contain outcomes of the notched-noise tests performed on some or all of the users of the system. The auditory filter processor 340 is configured to query the database to generate and/or update an empirical model (e.g., i.e., a probabilistic model for auditory filters for the user) of the prior distribution of potential auditory filter parameters. For example, the probabilistic model may be generated based on notched-noise test results of a large pool of users, for example, some or all the users of an auditory filter system, such as auditory filter fitting system 100 shown in FIG. 1. The probabilistic model may be updated based on, for example, a user response to a notched-noise test, a sampling from the database of notched-noise test results of other users with a similar hearing profile to the user, or both. The auditory filter processor 340 is configured to transmit the probabilistic model of auditory filters to the signal selector 350. The auditory filter processor 340 may transmit the probabilistic model of auditory filters to the signal selector 350 directly or via the processor 310. In some examples, the auditory filter processor 340 may be combined with the processor 310.

The signal selector 350 is configured to receive the probabilistic model of auditory filters and select a signal to test. The signal selector 350 is configured to use a Bayesian optimal experimental design to determine the next notched-noise test signal parameters to maximize the expected information gain of the test. For example, the signal to test is selected based on a determined level of the signal to reduce auditory filter uncertainty. In an example, a signal that is determined to have the highest reduction of auditory filter uncertainty is selected. The signal parameters may then be transmitted to the hearing device, for example, using the transceiver 320 and antenna 330.

The processor 310 may be coupled to, and may receive user input data from, the speaker/microphone 360, the display/touch interface 370 (e.g., a liquid crystal display (LCD) display unit or organic light-emitting diode (OLED) display unit), or both. The processor 310 may also output data to the speaker/microphone 360, the display/touch interface 370, or both. In addition, the processor 310 may access information from, and store data in, any type of suitable memory, such as the memory 380. The memory 380 may include RAM, ROM, a hard disk, a SIM card, a memory stick, an SD memory card, or any other type of memory storage device. In an embodiment, the processor 310 may access information from, and store data in, memory that is not physically located on the computing device 300, such as on the database.

The processor 310 may receive power from the power source 390, and may be configured to distribute and/or control the power to the other components of the computing device 300. The power source 390 may be any suitable device for powering the computing device 300. For example, the power source 390 may include one or more dry cell batteries (e.g., NiCd, NiZn, NiMH, Li-ion), solar cells, fuel cells, and the like.

Figure 4:
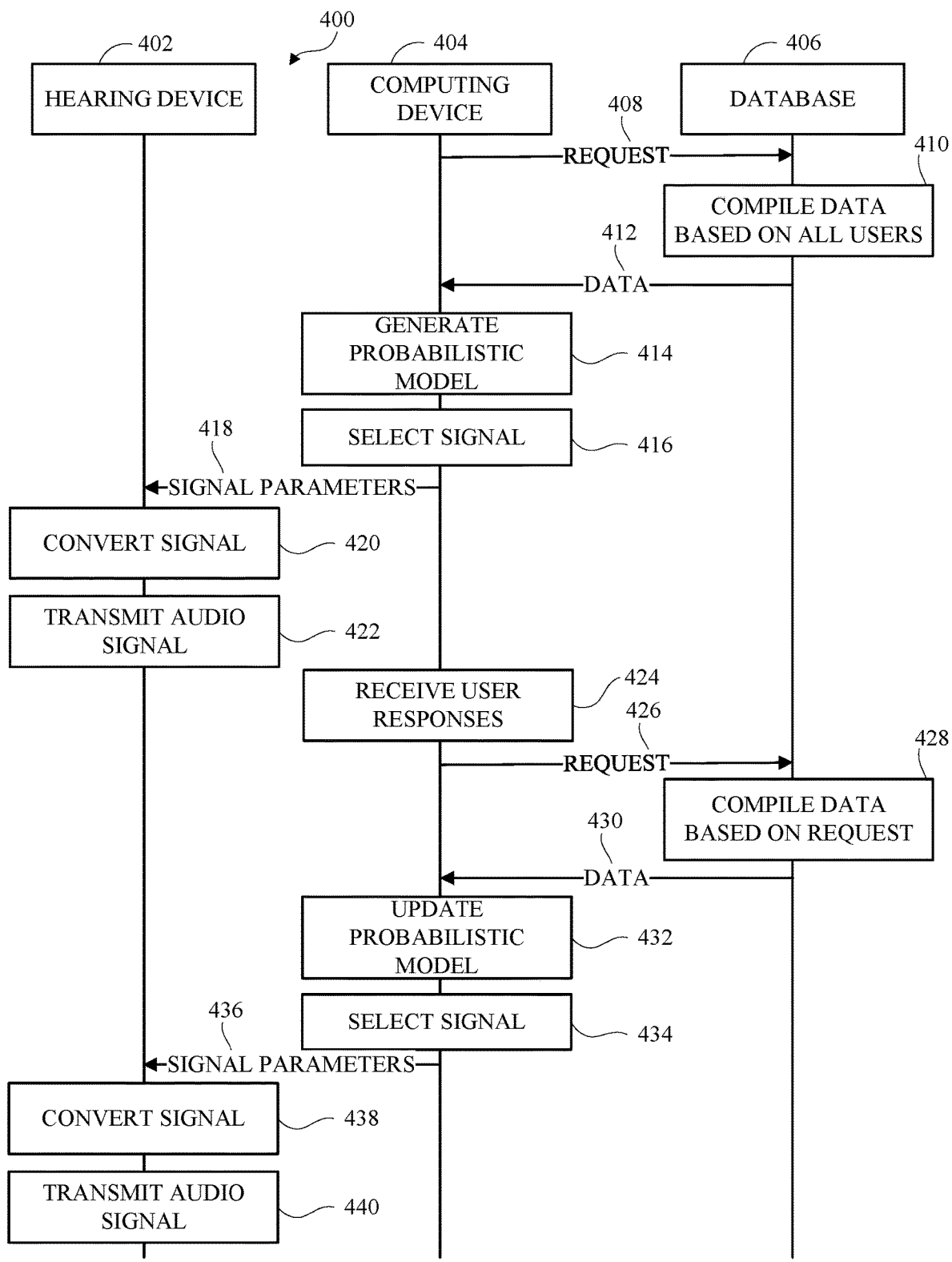
FIG. 4 is a swim lane diagram of an example of an auditory filter fitting workflow.

FIG. 4 is a swim lane diagram of an example of an auditory filter fitting workflow 400. The auditory filter fitting workflow 400 includes a hearing device 402, a computing device 404, and a database 406. The hearing device 402 may be the hearing device 200 shown in FIG. 2. The computing device 406 may be the computing device 300 shown in FIG. 3. The database 406 may be the database 130 shown in FIG. 1.

As shown in FIG. 4, the computing device 404 is configured to transmit a request 408 to the database 406. The request 408 may be a query for notched-noise test results of all the users of the system. The database 406 is configured to receive the request 408 and compile data 410 based on all users in response to the request 408. The database 406 is configured to transmit the data 412 compiled by the database 406 to the computing device 404.

The computing device 404 is configured to receive the data 412 and generate 414 a probabilistic model. The probabilistic model is generated based on the data 412. The probabilistic model may include a prior distribution of potential auditory filter parameters. The prior distribution of potential auditory filter parameters may be referred to herein as a "prior." The computing device 404 is configured to select 416 a signal to test. The signal to test may be notched-noise tests/measurements to perform on the user based on outcomes of previous tests done on the user as well as tests performed on other users in such a way as to minimize the number of tests that need to be performed in total for a particular user. In an example, the signal to test may be selected using a Bayesian optimal experimental design where the prior is based on both the current user's previous test results and on test results of other users with similar test results. The signal may be selected based on a determined level of the signal to reduce auditory filter uncertainty. In an example, a signal that is determined to have the highest reduction of auditory filter uncertainty is selected. The signal parameters 418 may then be transmitted to the hearing device 402.

The hearing device 402 is configured to receive the signal parameters 418 and convert 420 the signal parameters 418 to an audio signal. The audio signal may be a notched-noise signal. The hearing device 402 may be configured to apply calibration parameters of the hearing device 402 to the audio signal and transmit 422 the audio signal via a speaker of the hearing device 402.

The computing device 404 is configured to receive 424 user responses. The user responses may be received as user input in response to the audio signal transmitted by the hearing device 402. The user input may include a touch or gesture input on a display of the computing device 404 or a voice input from a microphone of the computing device 404. The computing device 404 may transmit a request 426 to the database 406 in response to the user responses. The request 426 may be a query for notched-noise test results of some the other users of the system (e.g., other users of the system that have a similar hearing profile to the user), previous notched-noise test results of the user, or both. The database 406 is configured to receive the request 426 and compile data 428 based on the request 426. The database 406 is configured to transmit the data 430 compiled by the database 406 to the computing device 404

The computing device 404 is configured to receive the data 430 and update 432 the probabilistic model. In some examples, the computing device 404 may use a deep neural network to encode the prior distribution by training to estimate the auditory filter parameters from the same notched-noise measurement data currently available in the fitting procedure to update the probabilistic model. The probabilistic model is updated based on the data 430, the received user responses, or both. The updated probabilistic model may include a subset of the prior distribution of potential auditory filter parameters. The computing device 404 is configured to select 434 a signal to test. The signal to test may be notched-noise tests/measurements to perform on the user based on outcomes of previous tests done on the user as well as a subset of tests performed on other users in such a way as to minimize the number of tests that need to be performed in total for a particular user. The subset of tests performed on other users may be determined based on the received user responses. In an example, the signal to test may be selected using a Bayesian optimal experimental design where the prior is based on both the current user's previous test results and on a subset of test results of other users with similar test results. The signal may be selected based on a determined level of the signal to reduce auditory filter uncertainty. In an example, a signal that is determined to have the highest reduction of auditory filter uncertainty is selected. The signal parameters 436 may then be transmitted to the hearing device 402.

The hearing device 402 is configured to receive the signal parameters 436 and convert 438 the signal parameters 436 to an audio signal. The audio signal may be a notched-noise signal. The hearing device 402 may be configured to apply calibration parameters of the hearing device 402 to the audio signal and transmit 4440 the audio signal via a speaker of the hearing device 402. The workflow 400 may continue receive 424 user responses and iteratively update the probabilistic model until a desirable auditory filter model is determined. The determination that the auditory filter model is desirable may be based on a difference in the improvement of the uncertainty in the model over time. For example, the process may be stopped when the model uncertainty stops decreasing below a certain threshold or the user decides that they are satisfied with the audio quality. The model uncertainty may be scaled to a range between 0 and 1, where 1 may be the uncertainty of the base prior distribution before the experiment begins and 0 may be a model with no uncertainty. The scaled uncertainty may represent the progress so that the scaling may be updated throughout the experiment, if needed, so that it is close to 0 at the end of the experiment. The decrease in uncertainty may be monitored throughout the experiment, and once the decrease is less than a threshold, the system may prompt the user and ask if they want to continue with the experiment. Throughout the fitting process, after each measurement, the system may display the updated uncertainty (i.e., a progress bar between 0 and 1 or a percentage between 0 and 100), and the user may determine whether to continue with the experiment with the option to resume at a later time if they are dissatisfied with the fitting. In some examples, the system may display a graph to show the user that provides a graphical representation of the rate of decrease in the model improvement. The system may be configured to predict the number of measurements needed to reach a certain level of uncertainty.

Figure 5:
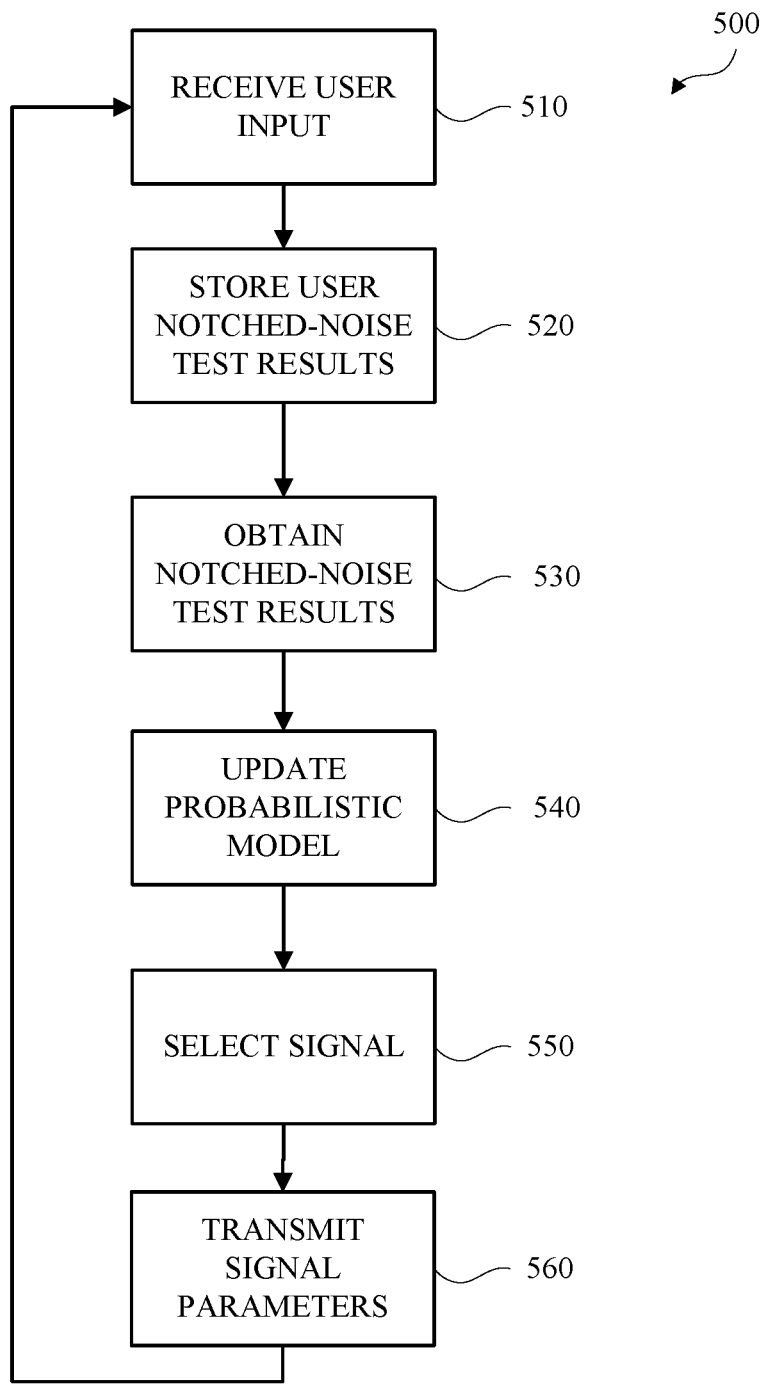
FIG. 5 is a flow diagram of an example of a method for auditory filter fitting.
Figure 6:
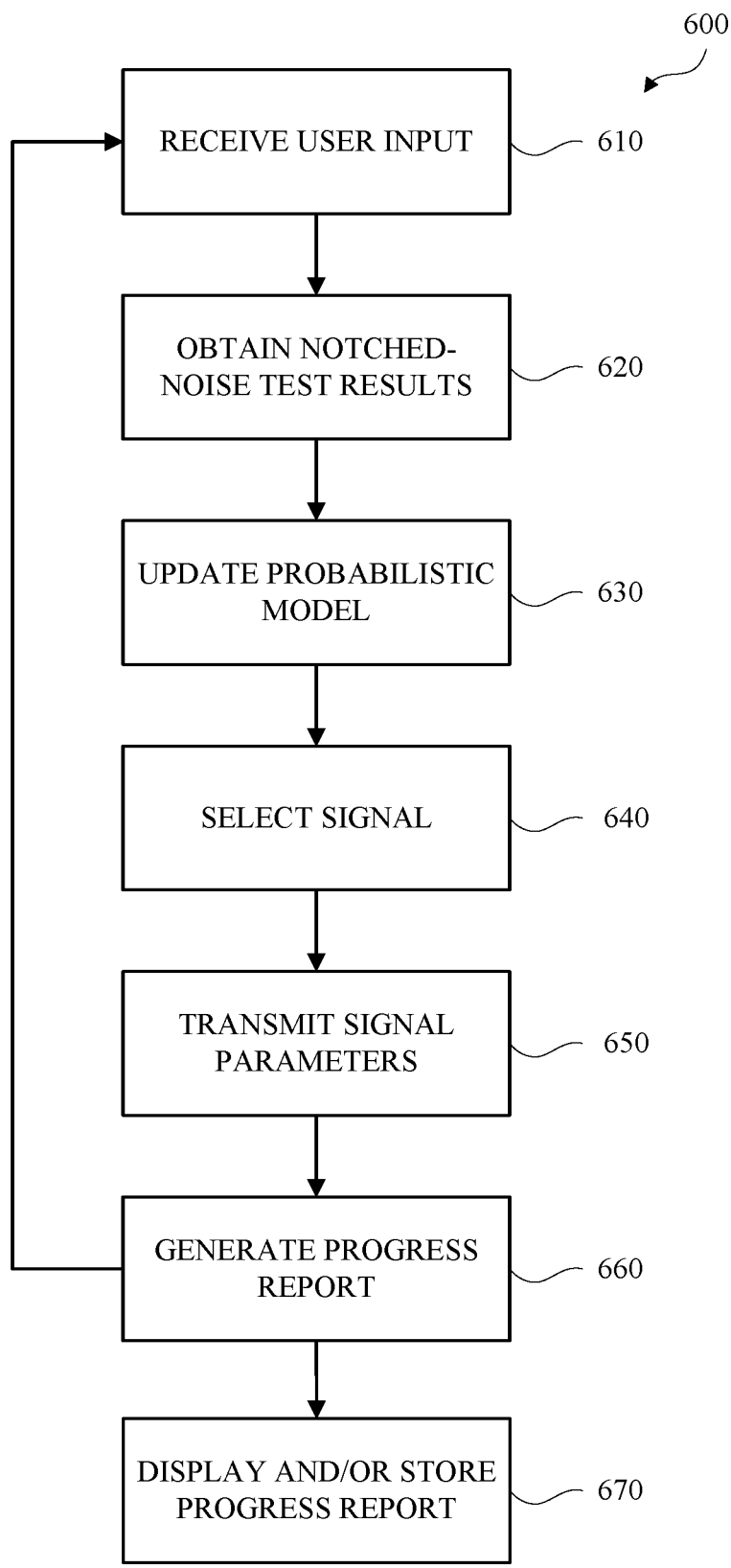
FIG. 6 is a flow diagram of another example of a method for auditory filter fitting.

To further describe some implementations in greater detail, reference is next made to examples of methods that may be performed by or using a system for auditory filter fitting for a hearing device. FIGS. 5 and 6 are flowcharts of examples of methods for auditory filter fitting for a hearing device. The methods can be executed using computing devices, such as the systems, hardware, and software described with respect to FIGS. 1 through 5. The methods can be performed, for example, by executing a machine-readable program or other computer-executable instructions, such as routines, instructions, programs, or other code. The steps, or operations, of the methods or other techniques, methods, processes, or algorithms described in connection with the implementations disclosed herein can be implemented directly in hardware, firmware, software executed by hardware, circuitry, or a combination thereof.

For simplicity of explanation, the methods are depicted and described herein as a series of steps or operations. However, the steps or operations in accordance with this disclosure can occur in various orders and/or concurrently. Additionally, other steps or operations not presented and described herein may be used. Furthermore, not all illustrated steps or operations may be required to implement a technique in accordance with the disclosed subject matter.

FIG. 5 is a flow diagram of an example of a method 500 for auditory filter fitting. At 510, the method 510 includes receiving user input. The user input may include a touch or gesture input on a display of a computing device, such as the computing device 110 shown in FIG. 1 or a voice input from a microphone of the computing device. The user input received may be based on a perception of an audible sound by the user, where the audible sound is provided to the user via a hearing device, such as the hearing device 200 shown in FIG. 2.

At 520, the method 500 includes storing user notched-noise test results. The notched-noise test results may be determined based on the input received from the user. The notched-noise test results may be stored in a memory of the computing device, the database, or both. In some embodiments, operation 520 may be optional.

At 530, the method 500 includes obtaining notched-noise test results. The obtained notched-noise test results may include the notched-noise test results of the user determined based on the user input, notched-noise test results of other users from a database, or both. The notched-noise test results of the user may be obtained from a local storage of a computing device, such as the memory 380 of the computing device 300 shown in FIG. 3. In some examples, the notched-noise test results of the user may be obtained from a database, such as the database 130 shown in FIG. 1. The notched-noise test results of the other users may be obtained from the database.

At 540, the method 500 includes updating the probabilistic model. The probabilistic model of the auditory filters for the user is updated based on the obtained notched-noise test results. The auditory filters may be asymmetrical such that the bandwidth is different on the side left of center and the side right of center. Accordingly, 3 parameters are required to describe each auditory filter instead of 2 parameters. The probabilistic model of the auditory filters for the user provides the most likely parameters of the auditory filters, an uncertainty value for each of the parameters of the auditory filters, or both. In some examples, a deep neural network can be used to encode the prior distribution by training to estimate the auditory filter parameters from the same notched-noise measurement data currently available in the fitting procedure (i.e. learning to estimate auditory filter parameters from limited data).

At 550, the method 500 includes selecting a signal to test. The signal to test may be notched-noise tests/measurements to perform on the user based on outcomes of previous tests done on the user as well as a subset of tests performed on other users in such a way as to minimize the number of tests that need to be performed in total for a particular user. The subset of tests performed on other users may be determined based on the received user input. For example, the notched-noise tests/measurements to perform on the user may be based on the obtained notched-noise test results of the user and the notched-noise test results of other users obtained from a database. In an example, the signal to test may be selected using a Bayesian optimal experimental design where the prior is based on both the current user's previous test results and on a subset of test results of other users with similar test results. The signal may be selected based on a determined level of the signal to reduce auditory filter uncertainty. In an example, a signal that is determined to have the highest reduction of auditory filter uncertainty is selected.

At 560, the method 500 includes transmitting signal parameters. The transmitted signal parameters are based on the selected signal to test. The signal parameters are transmitted to a hearing device, such as the hearing device 200 shown in FIG. 2 for output as an audio signal to the user to obtain a user response. The method returns to operation 510 to receive another user response such that the method 500 repeats to iteratively update and refine the probabilistic model until a desirable auditory filter model is determined.

FIG. 6 is a flow diagram of another example of a method 600 for auditory filter fitting. At 610, the method 600 includes receiving a user input. The user input may include a touch or gesture input on a display of a computing device, such as the computing device 110 shown in FIG. 1 or a voice input from a microphone of the computing device. The user input received may be based on a perception of an audible sound by the user, where the audible sound is provided to the user via a hearing device, such as the hearing device 200 shown in FIG. 2.

At 620, the method 600 includes obtaining notched-noise test results. The obtained notched-noise test results may include the notched-noise test results of the user determined based on the user input, notched-noise test results of other users from a database, or both. The notched-noise test results of the user may be obtained from a local storage of a computing device, such as the memory 380 of the computing device 300 shown in FIG. 3. In some examples, the notched-noise test results of the user may be obtained from a database, such as the database 130 shown in FIG. 1. The notched-noise test results of the other users may be obtained from the database.

At 630, the method 600 includes updating the probabilistic model. The probabilistic model of the auditory filters for the user is updated based on the obtained notched-noise test results. The probabilistic model of the auditory filters for the user provides the most likely parameters of the auditory filters, an uncertainty value for each of the parameters of the auditory filters, or both. In some examples, a deep neural network can be used to encode the prior distribution by training to estimate the auditory filter parameters from the same notched-noise measurement data currently available in the fitting procedure (i.e. learning to estimate auditory filter parameters from limited data).

At 640, the method 600 includes selecting a signal to test. The signal to test may be notched-noise tests/measurements to perform on the user based on outcomes of previous tests done on the user as well as a subset of tests performed on other users in such a way as to minimize the number of tests that need to be performed in total for a particular user. The subset of tests performed on other users may be determined based on the received user input. For example, the notched-noise tests/measurements to perform on the user may be based on the obtained notched-noise test results of the user and the notched-noise test results of other users obtained from a database. In an example, the signal to test may be selected using a Bayesian optimal experimental design where the prior is based on both the current user's previous test results and on a subset of test results of other users with similar test results. The signal may be selected based on a determined level of the signal to reduce auditory filter uncertainty. In an example, a signal that is determined to have the highest reduction of auditory filter uncertainty is selected.

At 650, the method 600 includes transmitting signal parameters. The transmitted signal parameters are based on the selected signal to test. The signal parameters are transmitted to a hearing device, such as the hearing device 200 shown in FIG. 2 for output as an audio signal to the user to obtain a user response.

At 660, the method 600 includes generating a progress report. The progress report may include a duration of time to complete the fitting process, a completed percentage of the process, a graphical representation of the completed percentage of the process (e.g., a status bar), or any combination thereof. The progress report may be based on the determined uncertainty value of one or more of the parameters of the auditory filter. The method returns to operation 610 to receive another user response such that the method 600 repeats to iteratively update and refine the probabilistic model until a desirable auditory filter model is determined.

At 670, the method 600 includes displaying and/or storing the progress report. The progress report may be displayed on a display of a computing device, such as the display/touch interface 370 of computing device 300 shown in FIG. 3. In some examples, the progress report may be stored in a memory, such as the memory 380 of computing device 300 shown in FIG. 3.

As used herein, the terminology "computer" or "computing device" includes any unit, or combination of units, capable of performing any method, or any portion or portions thereof, disclosed herein.

As used herein, the terminology "processor" indicates one or more processors, such as one or more special purpose processors, one or more digital signal processors, one or more microprocessors, one or more controllers, one or more microcontrollers, one or more application processors, one or more central processing units (CPU)s, one or more graphics processing units (GPU)s, one or more digital signal processors (DSP)s, one or more application specific integrated circuits (ASIC)s, one or more application specific standard products, one or more field programmable gate arrays, any other type or combination of integrated circuits, one or more state machines, cloud-based computing processors, or any combination thereof.

As used herein, the terminology "memory" indicates any non-transitory computer-usable or computer-readable medium or device that can tangibly contain, store, communicate, or transport any signal or information that may be used by or in connection with any processor. For example, a memory may be one or more read only memories (ROM), one or more random access memories (RAM), one or more registers, low power double data rate (LPDDR) memories, one or more cache memories, one or more semiconductor memory devices, one or more magnetic media, one or more optical media, one or more magneto-optical media, or any combination thereof.

As used herein, the terminology "instructions" may include directions or expressions for performing any method, or any portion or portions thereof, disclosed herein, and may be realized in hardware, software, cloud-based computing environment(s), or any combination thereof. For example, instructions may be implemented as information, such as a computer program, stored in memory that may be executed by a processor to perform any of the respective methods, algorithms, aspects, or combinations thereof, as described herein. Instructions, or a portion thereof, may be implemented as a special purpose processor, or circuitry, that may include specialized hardware for carrying out any of the methods, algorithms, aspects, or combinations thereof, as described herein. In some implementations, portions of the instructions may be distributed across multiple processors on a single device, on multiple devices, which may communicate directly or across a network such as a local area network, a wide area network, the Internet, or a combination thereof.

As used herein, the terminology "determine" and "identify," or any variations thereof, includes selecting, ascertaining, computing, looking up, receiving, determining, establishing, obtaining, or otherwise identifying or determining in any manner whatsoever using one or more of the devices and methods shown and described herein.

As used herein, the terminology "example," "embodiment," "implementation," "aspect," "feature," or "element" indicates serving as an example, instance, or illustration. Unless expressly indicated, any example, embodiment, implementation, aspect, feature, or element is independent of each other example, embodiment, implementation, aspect, feature, or element and may be used in combination with any other example, embodiment, implementation, aspect, feature, or element.

As used herein, the terminology "or" is intended to mean an inclusive "or" rather than an exclusive "or." That is, unless specified otherwise, or clear from context, "X includes A or B" is intended to indicate any of the natural inclusive permutations. That is, if X includes A; X includes B; or X includes both A and B, then "X includes A or B" is satisfied under any of the foregoing instances. In addition, the articles "a" and "an" as used in this application and the appended claims should generally be construed to mean "one or more" unless specified otherwise or clear from the context to be directed to a singular form.

Further, for simplicity of explanation, although the figures and descriptions herein may include sequences or series of steps or stages, elements of the methods disclosed herein may occur in various orders or concurrently. Additionally, elements of the methods disclosed herein may occur with other elements not explicitly presented and described herein. Furthermore, not all elements of the methods described herein may be required to implement a method in accordance with this disclosure. Although aspects, features, and elements are described herein in particular combinations, each aspect, feature, or element may be used independently or in various combinations with or without other aspects, features, and elements.

What is claimed is:

1. A system comprising:
    a database configured to store notched-noise test results of a plurality of users;
    a computing device configured to:
        obtain the notched-noise test results of the plurality of users;
        generate a probabilistic model of auditory filters based on the notched-noise test results of the plurality of users;
        select a signal to test based on the probabilistic model of auditory filters;
        transmit signal parameters based on the selected signal to test;
        receive a user response in response to the audio signal; and
        update the probabilistic model of auditory filters based on the received user response and notched-noise test results of a subset of the plurality of users, and
    a hearing device configured to:
        receive the signal parameters;
        convert the signal parameters to an audio signal; and
        transmit the audio signal.

2. The system of claim 1, wherein the subset of the plurality of users is determined based on the received user response.

3. The system of claim 1, wherein the audio signal is a notched-noise signal.

4. The system of claim 1, wherein the computing device is further configured to use a Bayesian optimal experimental design to select the signal to test.

5. A computing device comprising:
    a processor configured to obtain notched-noise test results of a plurality of users from a database;
    an auditory filter processor configured to generate a probabilistic model of auditory filters based on the notched-noise test results of the plurality of users;
    a signal selector configured to select a test signal based on the probabilistic model of auditory filters;
    a transmitter configured to transmit signal parameters based on the selected test signal;
    an interface configured to obtain a user response, wherein the auditory filter processor is further configured to update the probabilistic model of auditory filters based on the user response and notched-noise test results of a subset of the plurality of users.

6. The computing device of claim 5, wherein the auditory filter processor is further configured to determine the subset of the plurality of users based on the user response.

7. The computing device of claim 5, wherein the signal selector is configured to use a Bayesian optimal experimental design to select the test signal.

8. The computing device of claim 5, wherein the test signal is selected based on a determined level of the test signal to reduce auditory filter uncertainty.

9. The computing device of claim 5, further comprising:
generating a progress report comprising at least one of: duration to time to complete a fitting process for the hearing device, a completed percentage of the fitting process, or a graphical representation of the completed percentage of the fitting process.

10. The computing device of claim 9, wherein the progress report is generated based on a determined uncertainty value of one or more of the signal parameters.

11. A method for use in a computing device, the method comprising:
obtaining notched-noise test results of a plurality of users from a database;
generating a probabilistic model of auditory filters based on the notched-noise test results of the plurality of users;
selecting a test signal based on the probabilistic model of auditory filters;
transmitting signal parameters based on the selected test signal;
obtaining a user response;
updating the probabilistic model of auditory filters based on the user response and notched-noise test results of a subset of the plurality of users.

12. The method of claim 11, further comprising:
determining the subset of the plurality of users based on the user response.

13. The method of claim 11, wherein selecting the test signal includes using a Bayesian optimal experimental design.

14. The method of claim 11, wherein the signal parameters are transmitted to a hearing device for auditory filter fitting of the hearing device.

15. The method of claim 11, wherein the test signal is selected based on a determined level of the test signal to reduce auditory filter uncertainty.

16. The method of claim 11, further comprising:
generating a progress report comprising at least one of: duration to time to complete a fitting process for the hearing device, a completed percentage of the fitting process, or a graphical representation of the completed percentage of the fitting process.

17. The method of claim 16, wherein the progress report is generated based on a determined uncertainty value of one or more of the signal parameters.

* * * * *